United States Patent [19]
Romanovskaya

[11] Patent Number: 4,823,802
[45] Date of Patent: Apr. 25, 1989

[54] DEVICE FOR MEASUREMENT OF ARTERIAL BLOOD PRESSURE

[75] Inventor: Antonina M. Romanovskaya, Moscow, U.S.S.R.

[73] Assignee: Vsesojuzny Nauchno-issledovatelsky i ispytatelny institut meditsinskoi Tekhniki, Moscow, U.S.S.R.

[21] Appl. No.: 34,420

[22] Filed: Apr. 3, 1987

[51] Int. Cl.$^4$ .............................................. A61B 5/02
[52] U.S. Cl. .................................... 128/688; 310/340
[58] Field of Search ................. 128/688; 310/340, 330

[56] References Cited

U.S. PATENT DOCUMENTS

| | | | |
|---|---|---|---|
| 3,202,962 | 8/1965 | Elston | 310/340 X |
| 3,230,402 | 1/1966 | Nightingale et al. | 310/340 X |
| 3,360,665 | 12/1967 | Boswell | 310/340 X |
| 4,443,730 | 4/1984 | Kitamura et al. | 310/330 |

FOREIGN PATENT DOCUMENTS 651786 3/1979 U.S.S.R. .

Primary Examiner—William E. Wayner
Attorney, Agent, or Firm—Burgess, Ryan & Wayne

[57] ABSTRACT

A device for measurement of arterial blood pressure, comprising a compression cuff with a manometer, and a pulse wave sensor interposed between the compression cuff and the patient's body surface and situated below the cuff axis square with the direction of the pulse wave propagation, said sensor being connected to a recorder and having a piezoelectric crystal plate one of whose working surfaces carries a first elastic current-conducting layer, while the other working surface of said plate carries a second elastic current-conducting layer, a first elastic electric-insulating layer being applied to the surface of the first elastic current-conducting layer, and a third elastic current-conducting layer is situated on the surface of said first electric-insulating layer.

14 Claims, 3 Drawing Sheets

DEVICE FOR MEASUREMENT OF ARTERIAL BLOOD PRESSURE

FIELD OF THE INVENTION

The present invention relates generally to medicine, namely, to diagnostic cardiologic techniques and has particular reference to devices for measurement of arterial blood pressure.

BACKGROUND ART

Known in the present state of the art is a device for measurement of arterial blood pressure (cf. SU, A, No. 651,786), comprising a compression cuff with a manometer and a cardiac sounds sensor interposed between the compression cuff and the patient's body surface below the cuff axis transverse with respect to the direction of motion of the pulse wave.

The cardiac sounds sensor comprises a casing, a piezoelectric crystal plate secured in the casing, and a contact element made fast at the centre of the piezoelectric crystal plate. Sound vibrations arising in body tissues in response to a pressure change in the compression cuff caused by propagation of the pulse waves, are picked up, through the contact element, by the piezoelectric crystal plate and are converted into electric signals, which are then applied to a recorder.

Disadvantages of the above mentioned device are that the cardiac sounds sensor features too low accuracy of measurement of arterial blood pressure due to the fact that it responses not only to a useful signal but also to false or spurious signals caused by any extraneous acoustic noice, pressure fluctuations in the cuff, or muscular contrations. In addition, the known sensor is inapplicable for measuring the arterial blood pressure in infants or preschool children, since the useful signal in them is too weak and cannot therefore be discriminated by the cardiac sounds sensor against a background of acoustic noise.

One more prior-art device for measurement of arterial blood pressure is known (cf. SU, A, No. 895,405) to comprise a compression cuff, a manometer, a pulse wave sensor interposed between the compression cuff and the patient's body surface below the cuff axis transverse with respect to the direction of the pulse wave propagation, and connected to a recorder.

The pulse wave sensor comprises a casing, a piezoelectric crystal plate one of whose working surfaces carries a first elastic current-conducting layer, while the other working surface of the piezoelectric crystal plate carries a second elastic current-conducting layer, which piezoelectric crystal plate is secured in the casing and is connected to a contact element.

When the pulse wave is propagated under the sensor, the contact element performs angular oscillations which are converted by the piezoelectric crystal plate into an electric signal proportional to the amplitude of the aforesaid oscillations, which signal is then delivered to the recorder.

Disadvantage of the known device for measurement of arterial blood pressure consists in that the pulse wave sensor has a casing whose interaction with the compression cuff and the patient's body might cause a noise or interfering signal, thus affecting adversely the accuracy of the arterial blood pressure measurement. Moreover, such a sensor features, as a rule, rather great dimensions which hinders its application for measure arterial blood pressure in infants or preschool children.

SUMMARY OF THE INVENTION

It is an object of the invention to provide higher accuracy of arterial blood pressure measurement.

It is another object of the invention to provide a possibility of measuring arterial blood pressure in infants or preschool children with an adequate accuracy.

It is one more object of the invention to provide better mechanical contact between the patient's body surface and the pulse wave sensor.

Said objects can be accomplished in a device for measurement of arterial blood pressure comprising a compression cuff with a manometer, and a pulse wave sensor interposed between the compression cuff and the patient's body surface and located below the cuff axis which is square with the direction of the pulse wave propoagation, said sensor being connected to a recorder and having a piezoelectric crystal plate one of whose working surfaces carries a first elastic current-conducting layer, while the other working surface of said plate carries a second elastic current-conducting layer, according to the invention, placed on the surface of the first elastic current-conducting layer is a first elastic electric-insulating layer on whose surface is put a third elastic current-conducting layer.

It is preferred that in a device for measurement of arterial blood pressure, according to the invention, placed on the surface of the second elastic current-conducting layer be a second elastic electric-insulating layer.

It is also preferred that in a device for measurement of an arterial blood pressure, according to the invention, placed on the surface of the second elastic electric-insulating layer be a fourth elastic electric-conducting layer.

The abovementioned embodiment of a pulse wave sensor makes it possible to use the entire surface of the piezoelectric crystal plate for representing the pulse wave during its propagation under the sensor, as well as to provide for good mechanical contact between the sensor and the patient's body surface, which in turn renders it possible to considerably increase the sensor sensitivity and substantially reduce the effect of noise interferences arising from pressure fluctuations in the compression cuff and from muscular contractions at the place of application of the pulse wave sensor, since such interferences act upon the entire surface of the piezoelectric crystal surface uniformly and causes no flexure thereof and hence no interference signal appears. this in turn makes it possible to reduce the overall dimensions of the pulse wave sensor. All This leads to a higher accuracy of measurement of arterial blood pressure in adults and renders possible such measurements in infants and preschool children.

It is likewise expedient that in a device for measurement of arterial blood pressure, according to the invention, a first or a second elastic current-conducting layer be composed of at least two portions arranged consecutively in a direction of the pulse wave propagation.

Such an embodiment of the pulse wave sensor allows one to substantially increase its interference immunity when measuring arterial blood pressure on patient's move, since the pulse wave will act on said portions in turn, and a signal featuring some additional characters will appear at the output of the pulse wave sensor.

It is also expedient that in a device for measurement of arterial blood pressure, according to the invention, any of the elastic current-conducting layers be provided with stiffening ribs arranged square with the direction of the pulse wave propagation.

It is also expedient that in a device for measurement of arterial blood pressure, according to the invention, any of the elastic electric-insulating layers be provided with stiffening ribs arranged square with the direction of the pulse wave propagation.

Provision of the stiffening ribs makes it possible to add to the interference immunity and mechanical strength of the pulse wave sensor.

BRIEF DESCRIPTION OF THE DRAWINGS

In what follows the invention will be illustrated by some specific exemplary embodiments thereof to be read with reference to the accompanying drawings, wherein.

DETAILED DESCRIPTION OF THE INVENTION

Let us consider some embodiments of the present invention.

Figure 1:
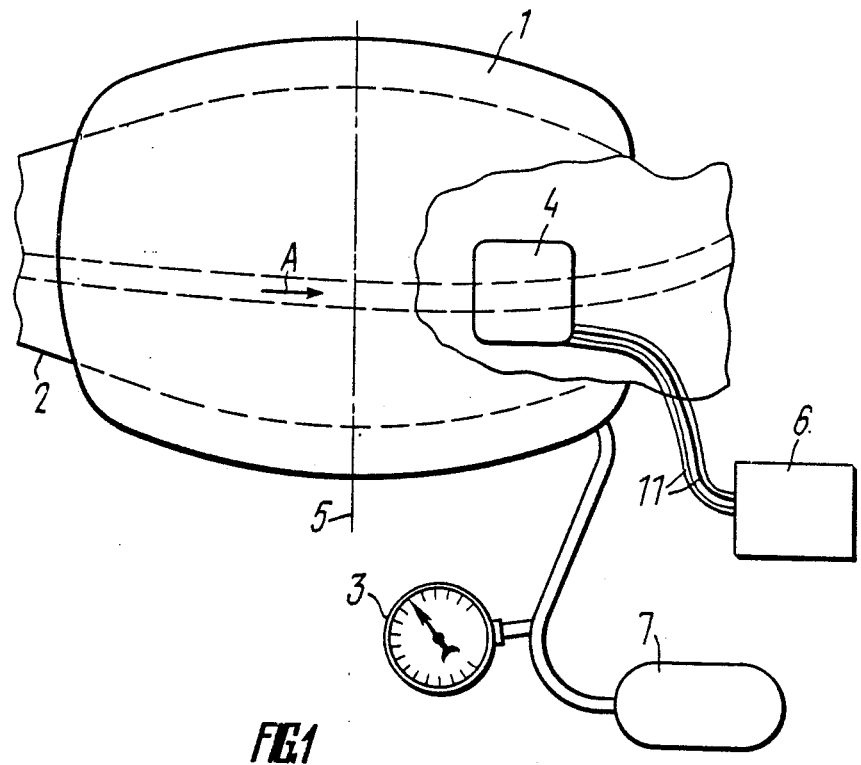
FIG. 1 is a general schematic view of a device for measurement of arterial blood pressure, according to the invention.
Figure 2:
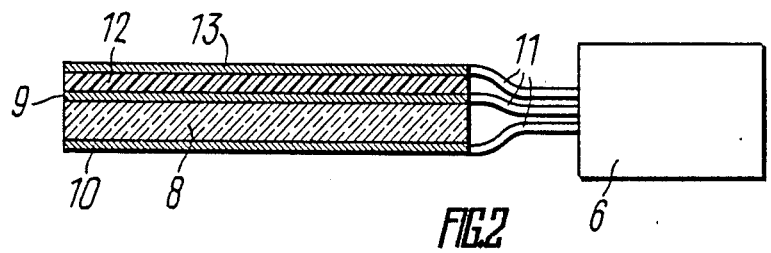
FIGS. 2 through 7 illustrate sectional views of various embodiments of a pulse wave sensor, according to the invention.

The device for measurement of arterial blood pressure (FIG. 1) comprises a compression cuff 1 adapted to be applied to a surface 2 of the patient's body, provided with a manometer 3 for pressure measurement in the compression cuff 1, a pulse wave sensor 4 interposed between the compression cuff 1 and the patient's body surface 2 and located below an axis 5 of the cuff square with the direction of the pulse wave propagation, said sensor being connected to a recorder 6 adapted to make record of a pulse wave. Used as the recorder 6 is a known recording instrument adapted to produce a running record of a signal delivered from the pulse wave sensor 4. The direction of the pulse wave propagation is indicated with an arrow A. An air blower 7 is connected to the compression cuff 1. The pulse wave sensor 4 (FIG. 2) comprises a piezoelectric crystal plate 8 one of whose working surfaces carries a first current-conducting layer 9, while the other working surface of the plate 8 carries a second elastic current-conducting layer 10. Both of the layers 9 and 10 are connected, through electric conductors 11, to the recorder 6.

Arterial blood pressure is measured as follows. Using the air blower 7 (FIG. 1) the pressure in the compression cuff 1 is increased until the blood flow along the artery is completely arrested. Then the pressure in the compression cuff 1 is gradually decreased, and the instant when a first pulse wave is propagated under the entire compression cuff 1 is determined with the aid of the pulse wave sensor 4 and the recorder 6. The pressure under the compression cuff 1 is so distributed that its maximum value occurs nearby the cuff cross axis 5. That is why the pulse wave sensor 4 should be positioned below the axis 5 when determining the instant when the pulse wave is propagated under the entire compression cuff 1.

At the instant when a first pulse wave is propagated under the pulse wave sensor 4, the pressure in the compression cuff 1 corresponds to the systolic value of the arterial blood pressure, and when the last pulse wave is being propagated, that is, when the artery is completely open, the pressure in the compression cuff 1 corresponds to the diastolic value of the arterial blood pressure.

Now let us consider the first embodiment (FIG. 2) of the pulse wave sesnor 4.

Placed on the surface of the first elastic current-conducting layer 9 is a first elastic electric-insulating layer 12 on whose surface is in turn located a third elastic current-conducting layer 13, which serves as a screen to protect the piezoelectric crystal plate 8 against external electromagnetic fields, whereas the first elastic electric-insulating layer 12 insulates the current-conducting layer 9 from the third elastic current-conducting layer 13.

Figure 3:
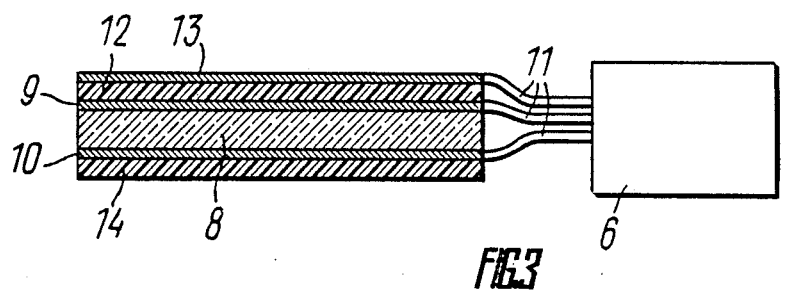

FIG. 3 represents a second embodiment of the pulse wave sensor 4. Placed on the surface of the second elastic current-conducting layer 10 is a second elastic electric-insulating layer 14 which serves to provide snug fitting of the pulse wave sensor 4 to the patient's body surface and insulate the current-conducting layer 10 of the piezoelectric crystal plate 8 from the ambient atmosphere.

Figure 4:
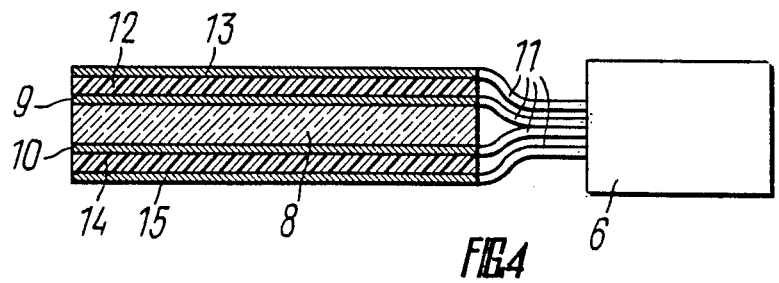

FIG. 4 illustrates one more embodiment of the pulse wave sensor 4 wherein a fourth elastic current-conducting layer 15 is applied to the surface of the second elastic electric-conducting layer 14 so as to screen the piezoelectric crystal plate 8 against external electromagnetic field.

With such a construction arrangement of the pulse wave sensor 4 there is utilized the entire surface of the piezoelectric crystal plate 8 to interact with the pulse wave as the latter is being propagated under the pulse wave sensor 4, and is reduced the effect of said sensor on the blood flow in the course of arterial blood pressure measurement.

As a result, sensitivity of the pulse wave sensor 4 is much increased, while the adverse effect of interferences caused by pressure fluctuations in the compression cuff 1, muscular contractions at the place of application of the pulse wave sensor 4 and external electromagnetic interferences, which in turn makes it possible to reduce the overall dimensions of the pulse wave sensor 4, to attain high accuracy of arterial blood pressure measurements in adults and to effect arterial blood pressure measurement in infants and preschool children.

Figure 5:
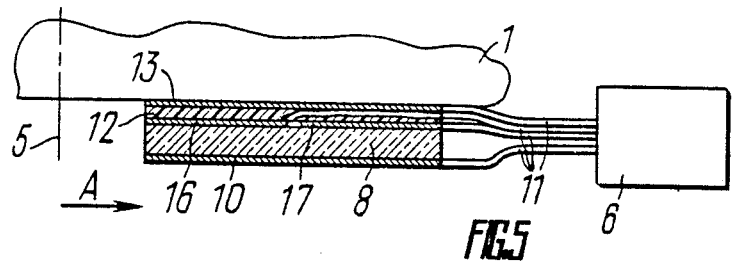

According to an embodiment of the pulse wave sensor 4 as depicted in FIG. 5, one of the elastic current-conducting layers, e.g., 9 is divided into two portions 16 and 17 arranged consecutively in the direction of the pulse wave propagation.

Figure 6:
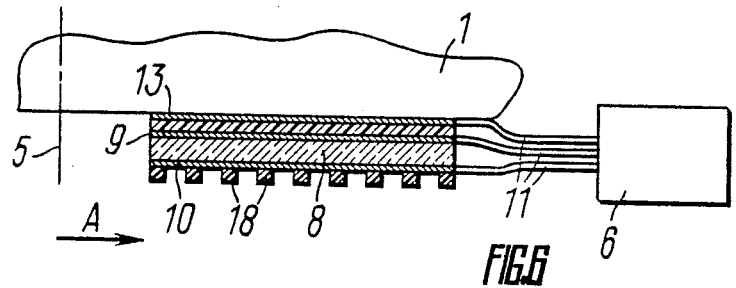
Figure 7:
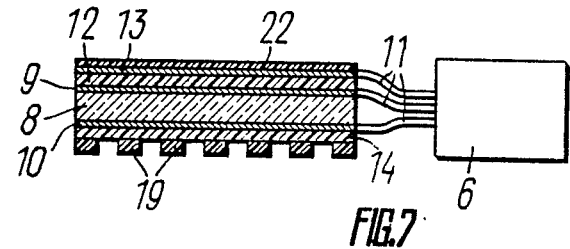
Figure 8:
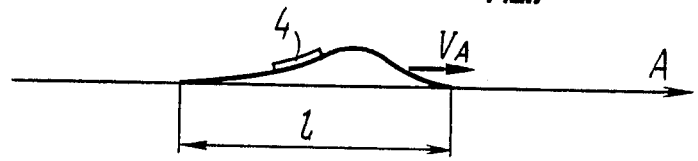
FIG. 8 illustrates how a pulse wave interacts with the pulse wave sensor.

FIGS. 6 and 7 represent further embodiments of the pulse wave sensor 4 provided with stiffening ribs 18, 19 arranged square with the direction of the pulse wave propagation. FIG. 6 illustrates the stiffening ribs 18 located on the current-conducting layer 10, while FIG. 7 shows the stiffening ribs 19 situated on the electric-insulating layer 14.

Provision of the stiffening ribs 18, 19 arranged as described above, prevents the piezoelectric crystal plate 8 from flexing in the directions other than that of the pulse wave propagation, which adds to the interference immunity of the pulse wave sensor 4. Moreover, the stiffening ribs 18, 19 add to the mechanical strength of the pulse wave sensor 4.

An electric signal is shaped as follows. A pulse wave having a length of '1', propagates at a velocity $V_A$ in a direction A. In this case a duration $\tau$ of the signal can be expressed as follows:

$$\tau = 1/V_A$$

Figure 9:
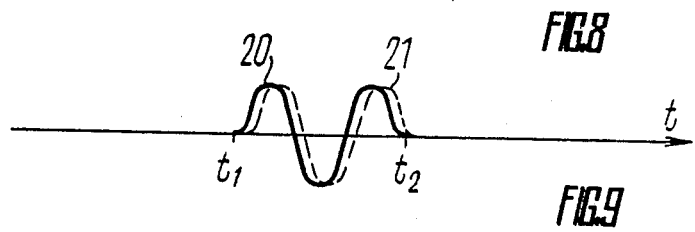
FIG. 9 illustrates a shape of an output signal of the pulse wave sensor when said wave is being propagated under said sensor.

The pulse wave sensor 4 experiences a number of consecutive flexures so that an electric signal is shaped at its output, as shown in FIG. 9, which is then delivered to the recorder 6. The duration of the signal can be expressed as follows:

$$\tau = t_2 - t_1,$$

where $t_1$—the instant of time characteristic of the beginning of propagation of a pulse wave under the pulse wave sensor 4;

$t_2$—the instant of time characteristic of the end of propagation of a pulse wave under the pulse wave sensor.

The pulse wave sensor 4 as illustrated in FIG. 5, makes it possible to obtain two or more signals 20, 21 time-shifted due to propagation of a pulse wave. Such a time shift can be used as an informative signal indicative of a pulse wave propagation under the pulse wave sensor 4, which makes it possible to increase the interference immunity of the pulse wave sensor 4 during arterial blood pressure measurement, thus attaining higher accuracy of arterial blood pressure measurement in adults and children.

The embodiments of the pulse wave sensor 4 illustrated in FIGS. 2 through 6 may have a moisture-proof layer 22 as illustrated in FIG. 7.

Use of the pulse wave sensor 4 as described hereinabove, in the device for measurement of arterial blood pressure, enables one to attain higher accuracy of arterial blood pressure measurement in infants and preschool children.

INDUSTRIAL APPLICABILITY

The invention is applicable for measurement of arterial blood pressure in patients of most diverse ages both in medical institutions and by patients themselves.

What is claimed is:

1. A casing-free device for measurement of arterial blood pressure, comprising:
   a compression cuff to be applied to a patient's body, said cuff having an axis arranged square with the direction of the pulse wave propagation;
   a manometer for measurement of pressure in said compression cuff, said manometer being connected to said compression cuff;
   a pulse wave sensor interposed between said compression cuff and the patient's body surface and located below said axis of the compression cuff, said sensor having an elastic piezoelectric crystal plate which comprises a first working surface and a second working surface, both of which freely receive a pulse wave directly over the entire area of the surface thereof;
   a first eleastic current-conducting layer situated on said first working surface;
   a second elastic current-conducting layer situated on said second working surface;
   a first electric-insulating layer situated on the surface of said first elastic current-conducting layer;
   a third elastic current-conducting layer situated on the surface of said first elastic electric-insulating layer;
   a recorder connected to said pulse wave sensor and adapted to make records of the pulse wave propagated.

2. A device as claimed in claim 1, comprising: a second elastic electric-insulating layer placed on the surface of said second elastic current-conducting layer.

3. A device as claimed in claim 2, comprising: a fourth elastic current-conducting layer located on the surface of said second elastic electric-insulating layer.

4. A device as claimed in claim 1 or 2, comprising: said first elastic current-conducting layer having at least two portions arranged consecutively in a direction of the pulse wave propagation.

5. A device as claimed in claim 1 or 2, comprising: said second elastic current-conducting layer, having at least two portions arranged consecutively in a direction of the pulse wave propagation.

6. A casing-free device for measurement of arterial blood pressure, comprising:
   a compression cuff to be applied to a patient's body, said cuff having an axis arranged square with the direction of the pulse wave propagation;
   a manometer for measurement of pressure in said compression cuff, said manometer being connected to said compression cuff;
   a pulse wave sensor interposed between said compression cuff and the patient's body surface and located below said axis of the compression cuff, said sensor having an elastic piezoelectric crystal plate which comprises a first working surface and a second working surface, both of which freely receive a pulse wave directly over the entire area of the surface thereof;
   a first eleastic current-conducting layer situated on said first working surface;
   a second elastic current-conducting layer situated on said second working surface;
   a first electric-insulating layer situated on the surface of said first elastic current-conducting layer;
   a third elastic current-conducting layer situated on the surface of said first elastic electric-insulating layer;
   a second elastic-insulating layer situated on the surface of said second elastic current-conducting layer;
   a fourth elastic current-conducting layer situated on the surface of said second elastic electric-insulating layer;
   a recorder connected to said pulse wave sensor and adapted to make records of the pulse waves propagated.

7. A device as claimed in claim 6, comprising:
   said first elastic current-conducting layer, comprising at least two portions arranged consecutively in the direction of the pulse wave propagation.

8. A device as claimed in claim 6, comprising,
   said second elastic current-conducting layer comprising at least two portions arranged consecutively in the direction of the pulse wave propagation.

9. A device for measurement of arterial blood pressure, comprising:

a compression cuff to be applied to a patient's body, said cuff having an axis arranged square with the direction of the pulse wave propagation;

a manometer for measurement of pressure in said compression cuff, said manometer being connected to said compression cuff;

a pulse wave sensor interposed between said compression cuff and the patient's body surface and located below said axis of the compression cuff, said sensor having a piezoelectric crystal plate which comprises a first working surface and a second working surface;

a first elastic current-conducting layer situated on said first working surface;

a second elastic current-conducting layer situated on said second working surface;

a first electric-insulating layer situated on the surface of said first elastic current-conducting layer;

a third elastic current-conducting layer applied to the surface of said first elastic electric-insulating layer;

a stiffening ribs arranged square with the direction of the pulse wave propagation and situated on any of said first through third elastic current-conducting layers;

a recorder connected to said pulse wave sensor and adapted to make records of the pulse waves propagated.

10. A device for measurement of arterial blood pressure, comprising:

a compression cuff to be applied to a patient's body, said cuff having an axis arranged square with the direction of the pulse wave propagation;

a manometer for measurement of pressure in said compression cuff, said manometer being connected to said compression cuff;

a pulse wave sensor interposed between said compression cuff and the patient's body surface and located below said axis of the compression cuff, said sensor having a piezoelectric crystal plate which comprises a first working surface and a second working surface;

a first elastic current-conducting layer situated on said first working surface;

a second elastic current-conducting layer situated on said second working surface;

a first electric-insulating layer situated on the surface of said first elastic current-conducting layer;

a third elastic current-conducting layer applied to the surface of said first elastic electric-insulating layer;

a second elastic electric-insulating layer placed on the surface of said second elastic current-conducting layer;

a fourth elastic current-conducting layer located on the surface of said second elastic electric-insulating layer;

stiffening ribs arranged square with the direction of the pulse wave propagation and situated on said fourth elastic current-conducting layer;

a recorder connected to said pulse wave sensor and adapted to make records of the pulse waves propagated.

11. A device for measurement of arterial blood pressure, comprising:

a compression cuff to be applied to a patient's body, said cuff having an axis arranged square with the direction of the pulse wave propagation;

a manometer for measurement of pressure in said compression cuff, said manometer being connected to said compression cuff;

a pulse wave sensor interposed between said compression cuff and the patient's body surface and located below said axis of the compression cuff, said sensor having a piezoelectric crystal plate which comprises a first working sruface and a second working surface;

a first elastic current-conducting layer situated on said first working surface;

a second elastic current-conducting layer situated on said second working surface;

a first electric-insulating layer situated on the surface of said first elastic current-conducting layer;

a third elastic current-conducting layer applied to the surface of said first elastic electric-insulating layer;

stiffening ribs arranged square with the direction of the pulse wave propagation and situated on said first elastic electric-insulating layer;

a recorder connected to said pulse wave sensor and adapted to make records of the pulse waves propagated.

12. A device for measurement of arterial blood pressure, comprising:

a compression cuff to be applied to a patient's body, said cuff having an axis arranged square with the direction of the pulse wave propagation;

a manometer for measurement of pressure in said compression cuff, said manometer being connected to said compression cuff;

a pulse wave sensor interposed between said compression cuff and the patient's body surface and located below said axis of the compression cuff, said sensor having a piezoelectric crystal plate which comprises a first working surface and a second working surface;

a first elastic current-conducting layer situated on said first working surface;

a second elastic current-conducting layer situated on said second working surface;

a first electric-insulating layer situated on the surface of said first elastic current-conducting layer;

a third elastic current-conducting layer applied to the surface of said first elastic electric-insulating layer;

a second elasti electric insulating layer placed on the surface of said second elastic current-conducting layer;

sixth stiffening ribs arranged square with the direction of the pulse wave propagation and situated on said second elastic electric-insulating layer;

a recorder connected to said pulse wave sensor and adapted to make records of the pulse waves propagated.

13. A device for measurement of arterial blood pressure, comprising:

a compression cuff to be applied to a patient's body, said cuff having an axis arranged square with the direction of the pulse wave propagation;

a manometer for measurement of pressure in said compression cuff, said manometer being connected to said compression cuff;

a pulse wave sensor interposed between said compression cuff and the patient's body surface and located below said axis of the compression cuff, said sensor having a piezoelectric crystal plate which comprises a first working surface and a second working surface;

a first elastic current-conducting layer situated on said first working surface;

a second elastic current-conducting layer situated on said second working surface;

a first electric-insulating layer situated on the surface of said first elastic current-conducting layer;

a third elastic current-conducting layer applied to the surface of said first elastic electric-insulating layer;

a second elastic electric-insulating layer placed on the surface of said second elstic current-conducting layer;

a fourth elastic current-conducting layer situated on the surface of said second elastic electric-insulating layer;

stiffening ribs arranged square with the direction of the pulse wave propagation and situated on any of said first through fourth elastic current-conducting layers;

a recorder connected to said pulse wave sensor and adapted to make records of the pulse waves propagated.

14. A device for measurement of arterial blood pressure, comprising:

a compression cuff to be applied to a patient's body, said cuff having an axis arranged square with the direction of the pulse wave propagation;

a manometer for measurement of pressure in said compression cuff, said manometer being connected to said compression cuff;

a pulse wave sensor interposed between said compression cuff and the patient's body surface and located below said axis of the compression cuff, said sensor having a piezoelectric crystal plate which comprises a first working surface and a second working surface;

a first elastic current-conducting layer situated on said first working surface;

a second elastic current-conducting layer situated on said second working surface;

a first electric-insulating layer situated on the surface of said first elastic current-conducting layer;

a third elastic current-conducting layer applied to the surface of said first elastic electric-insulating layer;

a second elastic electric-insulating layer placed on the surface of said second elastic current-conducting layer a fourth elastic current-conducting layer situated on the surface of said second elastic electric-insulating layer;

stiffening ribs arranged square with the direction of the pulse wave propagation and situated on any of said first and second elastic electric-insulating layer;

a recording connected to said pulse wave sensor and adapted to make records of the pulse waves propagated.

* * * * *